(12) United States Patent
Sethi et al.

(10) Patent No.: US 8,814,791 B2
(45) Date of Patent: Aug. 26, 2014

(54) SYSTEMS AND METHODS FOR MONITORING PAIN MANAGEMENT

(75) Inventors: Rakesh Sethi, Vancouver (CA); Paul Stanley Addison, Edinburgh (GB); James N. Watson, Dunfermline (GB); Paul A. Edney, Boulder, CO (US)

(73) Assignee: Nellcor Puritan Bennett Ireland, Galway (IE)

( * ) Notice: Subject to any disclaimer, the term of this patent is extended or adjusted under 35 U.S.C. 154(b) by 574 days.

(21) Appl. No.: 12/750,935

(22) Filed: Mar. 31, 2010

(65) Prior Publication Data

US 2010/0249543 A1  Sep. 30, 2010

Related U.S. Application Data

(60) Provisional application No. 61/165,349, filed on Mar. 31, 2009.

(51) Int. Cl.
*A61B 5/00* (2006.01)
*G06F 19/00* (2011.01)

(52) U.S. Cl.
CPC .................................. *G06F 19/34* (2013.01)
USPC ............................ 600/301; 600/300; 600/324

(58) Field of Classification Search
USPC .................................. 600/300–301, 323–324
See application file for complete search history.

(56) References Cited

U.S. PATENT DOCUMENTS

| | | | |
|---|---|---|---|
| 5,361,758 A | 11/1994 | Hall et al. | |
| 7,225,813 B2 * | 6/2007 | Easter ........................... | 128/898 |
| 7,407,485 B2 | 8/2008 | Huiku | |
| 7,407,486 B2 | 8/2008 | Huiku et al. | |
| 7,925,338 B2 | 4/2011 | Huiku | |
| 8,028,694 B2 * | 10/2011 | Hickle ...................... | 128/203.14 |
| 2003/0018241 A1 | 1/2003 | Mannheimer | |
| 2003/0078480 A1 | 4/2003 | Claure et al. | |
| 2003/0163033 A1 | 8/2003 | Dekker | |
| 2004/0015091 A1 | 1/2004 | Greenwald et al. | |
| 2004/0111014 A1 * | 6/2004 | Hickle ........................... | 600/300 |
| 2004/0260186 A1 | 12/2004 | Dekker | |
| 2005/0112325 A1 * | 5/2005 | Hickle ........................... | 428/141 |
| 2005/0272984 A1 | 12/2005 | Huiku | |
| 2006/0093785 A1 * | 5/2006 | Hickle ........................... | 428/121 |
| 2006/0217615 A1 * | 9/2006 | Huiku et al. .................. | 600/484 |
| 2006/0258921 A1 | 11/2006 | Addison et al. | |
| 2007/0010723 A1 | 1/2007 | Uutela et al. | |

(Continued)

FOREIGN PATENT DOCUMENTS

| JP | 2000-107141 | 4/2000 |
|---|---|---|
| WO | WO0154575 | 8/2001 |

OTHER PUBLICATIONS

Yansun Xu et al., "Wavelet Transform Domain Filters: A Spatially Selective Noise Filtration Technique", IEEE Transactions on Image Processing, Nov. 1994, vol. 3, No. 6, pp. 747-758,.

(Continued)

*Primary Examiner* — Bill Thomson
*Assistant Examiner* — Bobby Soriano
(74) *Attorney, Agent, or Firm* — Shvarts & Leiz LLP

(57) ABSTRACT

The present disclosure relates to systems and methods for monitoring pain management using measurements of physiological parameters based on a PPG signal. A reference physiological parameter may be compared against a later measurement to identify a change in condition that may indicate a pain management problem.

20 Claims, 14 Drawing Sheets

(56) References Cited

U.S. PATENT DOCUMENTS

| | | | |
|---|---|---|---|
| 2007/0073124 A1* | 3/2007 | Li et al. | 600/323 |
| 2007/0191789 A1* | 8/2007 | Hickle | 604/257 |
| 2008/0139907 A1 | 6/2008 | Rao et al. | |
| 2008/0146893 A1* | 6/2008 | Levendowski et al. | 600/300 |
| 2008/0167540 A1 | 7/2008 | Korhonen et al. | |
| 2008/0249382 A1 | 10/2008 | Oh et al. | |
| 2009/0018409 A1* | 1/2009 | Banet et al. | 600/301 |
| 2009/0105556 A1* | 4/2009 | Fricke et al. | 600/301 |
| 2009/0324034 A1 | 12/2009 | Watson et al. | |
| 2009/0326353 A1 | 12/2009 | Watson et al. | |
| 2009/0326386 A1 | 12/2009 | Sethi et al. | |
| 2009/0326393 A1 | 12/2009 | Sethi et al. | |
| 2009/0326402 A1 | 12/2009 | Addison et al. | |
| 2010/0185068 A1 | 7/2010 | Park et al. | |
| 2010/0228103 A1* | 9/2010 | Schecter | 600/301 |
| 2010/0249544 A1 | 9/2010 | Sethi et al. | |
| 2010/0249555 A1 | 9/2010 | Sethi et al. | |
| 2010/0249556 A1 | 9/2010 | Sethi et al. | |
| 2011/0124979 A1* | 5/2011 | Heneghan et al. | 600/301 |
| 2011/0137134 A1 | 6/2011 | Hemmerling et al. | |

OTHER PUBLICATIONS

Zhecun Song et al., "Simulation of Pulse Signal Based on Wavelet Transform," Management Science and Electronic Commerce (AIMSEC), 2011, 2nd International Conference on Artificial Intelligence. Aug. 8-10, 2011, pp. 4307-4310.

Amara Graps, "An Introduction to Wavelets", Institute of Electrical and Electronics Engineers/IEEE Computational Science and Engineering, vol. 2, No. 2, Summer 1995, IEEE Computer Society, Los Alamitos, CA, USA. pp. 1-18.

Continuous Wavelet Transform Wikipedia, the free encyclopedia. Downloaded from http://en.wikipedia.org/wiki/Continous_wavelet_transform on Jun. 14, 2012, Wikimedia Foundation, pp. 1-4.

Non Final Office Action for U.S. Appl. No. 12/750,950 mailed on Dec. 23, 2011; 11 pages.

Notice of Allowance for U.S. Appl. No. 12/750,950 mailed on Sep. 5, 2012; 10 pages.

Non Final Office Action for U.S. Appl. No. 12/750,944 mailed on Aug. 7, 2012; 6 pages.

Non Final Office Action for U.S. Appl. No. 12/750,932 mailed on Jul. 5, 2012; 16 pages.

Addison, Paul S., The Illustrated Wavelet Transform Handbook, Taylor & Francis Group, 2002, 353 pages.

Amara Graps, "Wavelet vs. Fourier Transforms" May 12, 2004, downloaded from http://www.amara.com/IEEEwave/IW_wave_vs_four.html on Jun. 14, 2012, pp. 1-3.

* cited by examiner

SYSTEMS AND METHODS FOR MONITORING PAIN MANAGEMENT

CROSS-REFERENCE TO RELATED APPLICATION

This application claims priority to U.S. Provisional Application No. 61/165,349, filed Mar. 31, 2009, and is incorporated by reference herein in its entirety.

SUMMARY

The present disclosure relates to pain management monitoring using one or more measurements of a patient's physiological condition that may be determined using a photoplethysmograph (PPG) signal.

In an embodiment, physiological parameters, such as one or more vital signs of a patient may be used to monitor effectiveness of pain management. For example, when a patient is sedated, anesthetized or otherwise provided pain medication, the patient may experience certain physiological effects. Other physiological effects may be experienced when the patient is subjected to pain. Accordingly, the effect of pain or pain medication may cause the patient's physiological parameters, such as blood pressure, pulse rate, respiration rate, respiration effort, or other parameter, alone or in combination, to change. These changes to the patient's physiological parameters may be used as a basis for determining whether a patient's pain is managed adequately. The embodiments described herein may be applicable for a wide range of pain management scenarios, but may be of particular use during treatment of an unconscious or sedated patient, a child, or other patient that may not be capable of communicating a pain management need.

In an embodiment, blood pressure may be calculated using a PPG signal based continuous non-invasive blood pressure (CNIBP) technique, further described herein, using one or more sensors. In an embodiment, respiration rate and respiration effort may be calculated by analyzing a PPG signal obtained using a sensor, such as a pulse oximeter. Other physiological parameters may also be used in accordance with the disclosure herein to provide comprehensive pain management monitoring.

In general, a change in one or more physiological parameters, such as blood pressure, respiration rate, respiration effort, or other parameter may provide an indication of effectiveness of pain management. For example, an increase in blood pressure for a sedated patient may indicate that a patient is experiencing pain. Typically, receipt of pain medication may result in vasodilation or a reduction in blood pressure, or both. Such effect can be identified by blood pressure monitoring. Similarly, a change in pulse rate, respiration rate or respiration effort, alone, or in combination with a change in blood pressure, may indicate a problem with pain management.

In an embodiment, a change in one or more physiological parameters may be used to identify a pain management problem that may require a remedy. In another embodiment, one or more physiological parameters may be monitored after pain medication or sedation is administered to determine effectiveness of a pain treatment. In another embodiment, a determined effectiveness of pain treatment may be used as a basis for administering future pain treatments. These embodiments are described in further detail herein.

DETAILED DESCRIPTION

Figure 1:
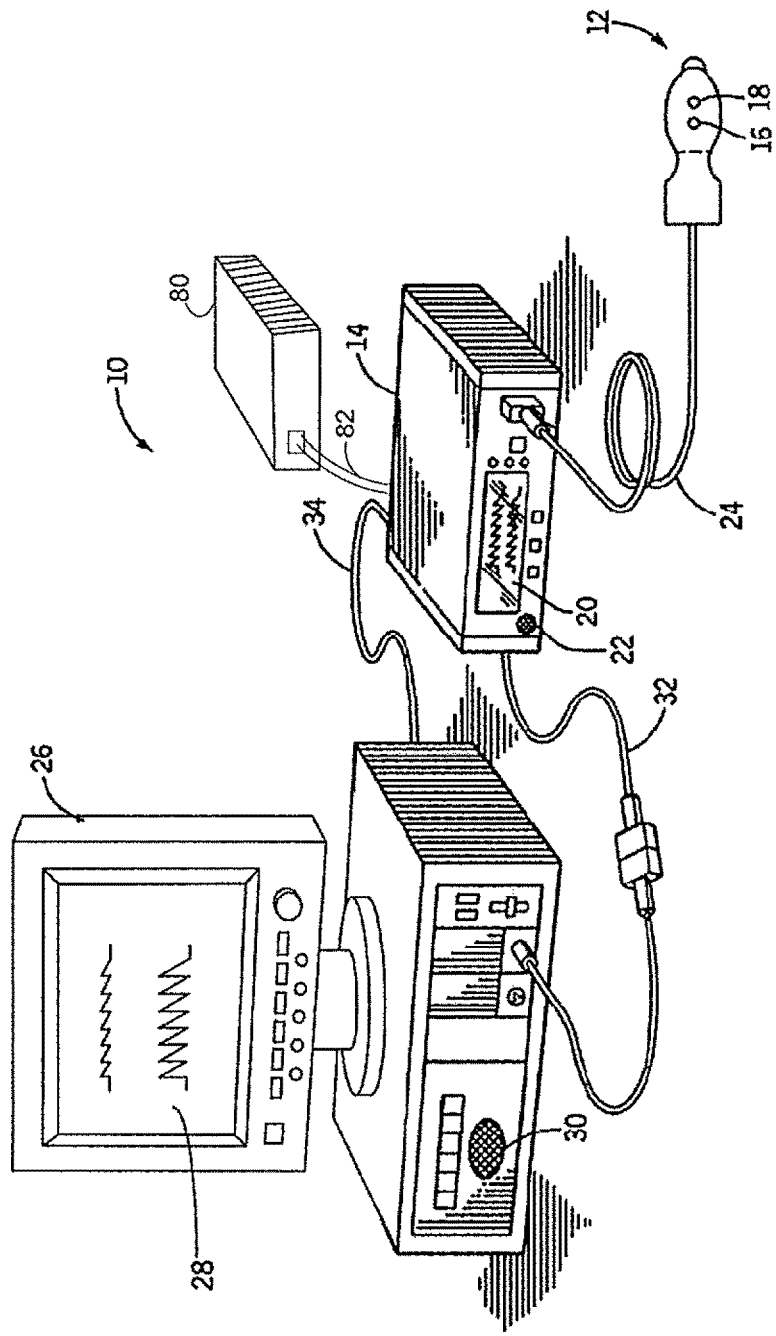
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I=\log I_o-(s\beta_o+(1-s)\beta_r)l \quad (2)$$

2. (2) is then differentiated with respect to time $$\frac{d\log I}{dt}=-(s\beta_o+(1-s)\beta_r)\frac{dl}{dt} \quad (3)$$

3. Red (3) is divided by IR (3)

$$\frac{d\log I(\lambda_R)/dt}{d\log I(\lambda_{IR})/dt}=\frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s=\frac{\frac{d\log I(\lambda_{IR})}{dt}\beta_r(\lambda_R)-\frac{d\log I(\lambda_R)}{dt}\beta_r(\lambda_{IR})}{\frac{d\log I(\lambda_R)}{dt}(\beta_o(\lambda_{IR})-\beta_r(\lambda_{IR}))-\frac{d\log I(\lambda_{IR})}{dt}(\beta_o(\lambda_R)-\beta_r(\lambda_R))}$$

Note in discrete time $$\frac{d\log I(\lambda,t)}{dt}\simeq \log I(\lambda,t_2)-\log I(\lambda,t_1)$$

Using log A−log B=log A/B, $$\frac{d\log I(\lambda,t)}{dt}\simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}}\simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)}=R \quad (5)$$

where R represents the "ratio of ratios." Solving (4) for s using (5) gives $$s=\frac{\beta_r(\lambda_R)-R\beta_r(\lambda_{IR})}{R(\beta_o(\lambda_{IR})-\beta_r(\lambda_{IR}))-\beta_o(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt}=\frac{dI/dt}{I} \quad (6)$$

now (5) becomes $$\frac{\frac{d\log I(\lambda_R)}{dt}}{\frac{d\log I(\lambda_{IR})}{dt}}\simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$=\frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$=R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR}) \quad (8)$$

$$y(t)=Rx(t)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury spygmomanometer and occluding cuff, a pressure sensor inserted directly into a suitable artery of a patient, or any other device or mechanism used to sense, measure, determine, or derive a reference blood pressure measurement. In some embodiments, calibration device 80 may include a manual input device (not shown) used by an operator to manually input reference or baseline blood pressure measurements obtained from some other source (e.g., an external invasive or non-invasive blood pressure measurement system). Calibration device 80 may also be used to provide reference or baseline measurements for respiration rate, respiration effort, or other physiological parameters.

In accordance with some embodiments, the reference blood pressure, respiration rate, respiration effort, or other measurements may be used to generate empirical data for one or multiple patients. In particular, the reference measurements may be used to provide coefficient information for the equations generated based on the empirical data that may be used to determine physiological parameter measurement using one or more techniques based on a PPG signal.

Calibration device 80 may also access reference blood pressure, respiration rate, respiration effort, or other measurements stored in memory (e.g., RAM, ROM, or a storage device). For example, in some embodiments, calibration device 80 may access reference measurements from a relational database stored within calibration device 80, monitor 14, or multi-parameter patient monitor 26. As described in more detail below, the reference measurements generated or accessed by calibration device 80 may be updated in real-time, resulting in a continuous source of reference measurements for use in continuous or periodic calibration, as well as for providing baseline references for certain calculations. Alternatively, reference measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference measurements may then be wirelessly transmitted to monitor 14 for use in calibration. In still other embodiments, calibration device 80 is completely integrated within monitor 14.

Figure 2:
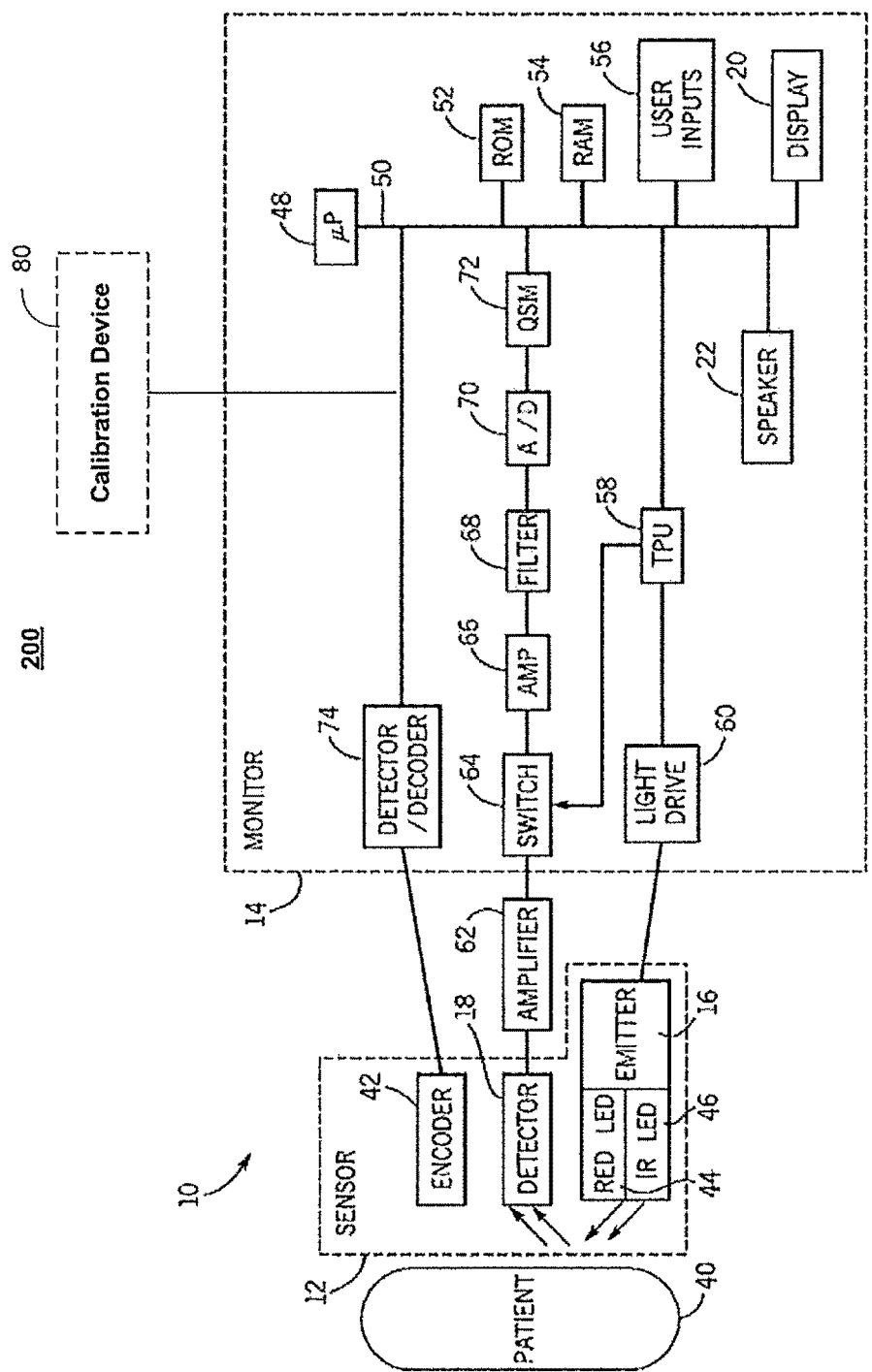
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. In addition, encoder 42 may include baseline or reference information for certain physiological parameters that may not be patient-specific. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, pain management information, reference information for physiological parameters, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

Various approaches have been used for monitoring the blood pressure of living subjects. One approach is to insert a pressure sensor directly into a suitable artery of the subject. The sensor may be connected to a suitable monitoring device by a lead which passes through the subject's skin. This approach may provide highly accurate and instantaneous blood pressure measurements, but is very invasive. A surgical procedure is generally required to introduce the pressure sensor, and the fistula through which the lead exits the subject's body can provide a pathway for infection.

Another approach to measuring blood pressure uses a sphygmomanometer. A typical sphygmomanometer has an occluding cuff capable of being wrapped around a subject's arm. A pump is used to inflate the cuff, and an aneroid or mercury gravity sphygmomanometer is used to measure the pressure in the cuff. Such devices are widely used in hospitals, but are not well adapted for providing continuous blood pressure monitoring.

Some continuous non-invasive blood pressure monitoring (CNIBP) techniques have been developed that involve the use of two probes or sensors positioned at two different locations on a subject's body. The elapsed time, T, between the arrival of corresponding points of a pulse signal at the two locations may then be determined using the two probes or sensors. The estimated blood pressure, p, may then be related to the elapsed time, T, by $$p = a + b \cdot \ln(T) \quad (9)$$

where a and b are constants that are dependent upon the nature of the subject and the signal detecting devices. Other blood pressure equations using elapsed time may also be used. These techniques may be referred to as differential pulse transit time (DPTT) based CNIBP.

In some embodiments, the constants a and b in equation (9) may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

The calibration may include performing calculations mathematically equivalent to $$a = c_1 + \frac{c_2(P_0 - c_1)}{\ln(T_0) + c_2} \quad (10)$$

and $$b = \frac{P_0 - c_1}{\ln(T_0) + c_2} \quad (11)$$

to obtain values for the constants a and b, where $c_1$ and $c_2$ are predetermined constants.

In other embodiments, determining the plurality of constant parameters in the multi-parameter equation (1) may include performing calculations mathematically equivalent to $$a = P_0 - (c_3 T_0 + c_4)\ln(T_0) \quad (12)$$

and $$b = c_3 T_0 + c_4 \quad (13)$$

where a and b are first and second parameters and $c_3$ and $c_4$ are predetermined constants.

In some embodiments, the multi-parameter equation (9) includes a non-linear function which is monotonically decreasing and concave upward in a manner specified by the constant parameters.

Continuous and non-invasive blood pressure monitoring using these techniques is described in Chen et al. U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

The use of multiple probes or sensors in non-invasive continuous blood pressure monitoring provides reliable results. However, in some instances, the use of multiple separate probes or sensors at different locations on the subject's body may be cumbersome, especially for a mobile subject. Moreover, one of the multiple probes or sensors may become detached from the subject, resulting in a disruption in the continuous monitoring of the patent's blood pressure. Accordingly, some techniques for continuously monitoring a subject's blood pressure use only a single probe or sensor. In some embodiments, the single probe or sensor may detect a photoplethysmograph (PPG) signal generated, for example, by a pulse oximeter. The PPG signal may then be analyzed and used to compute a time difference between two or more characteristic points in the PPG signal. From this time difference, reliable and accurate blood pressure measurements may be computed on a continuous or periodic basis. This technique is described in more detail in U.S. patent application Ser. No. 12/242,238, filed Sep. 30, 2008, entitled "SYSTEMS AND METHODS FOR NON-INVASIVE BLOOD PRESSURE MONITORING," which is incorporated by reference herein in its entirety. In some embodiments, blood pressure measurements may be determined based on pulses in a PPG signal detected by a single sensor, for example, by measuring the area under a pulse or a portion of the pulse in the PPG signal. This technique is described in more detail in U.S. patent application Ser. No. 12/242,867, filed Sep. 30, 2008, entitled "SYSTEMS AND METHODS FOR NON-INVASIVE CONTINUOUS BLOOD PRESSURE DETERMINATION," which is incorporated by reference herein in its entirety.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3A:
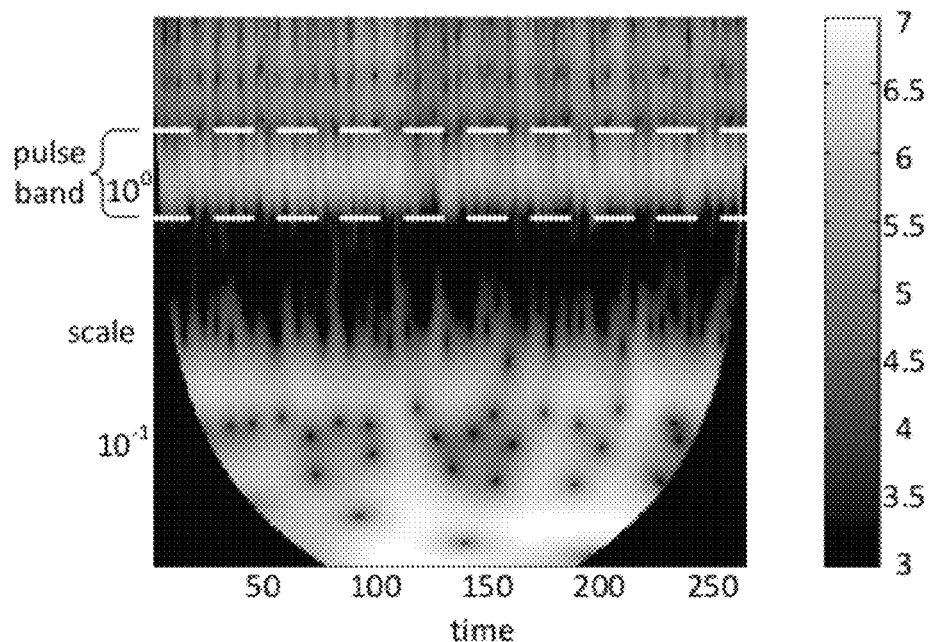
FIGS. 3(a) and 3(b) show illustrative views of a scalogram derived from a PPG signal in accordance with an embodiment.
Figure 3B:
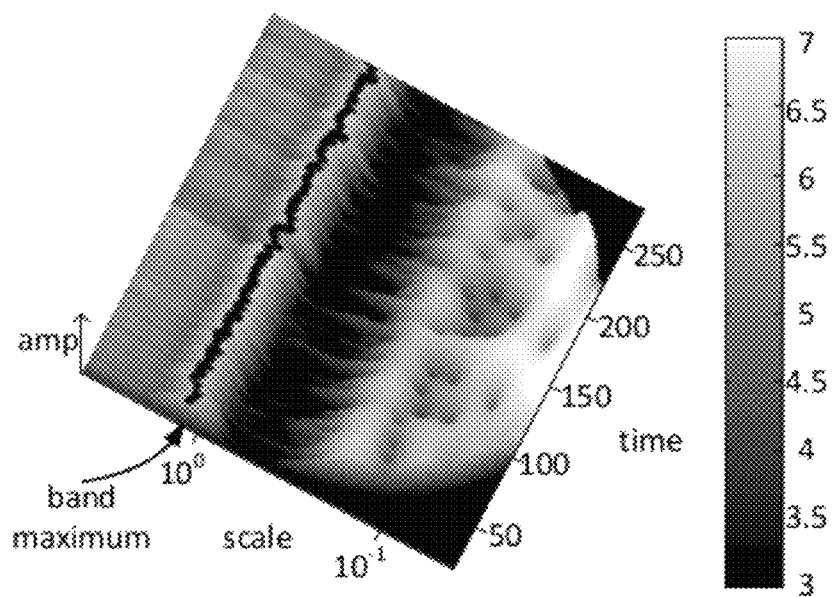

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
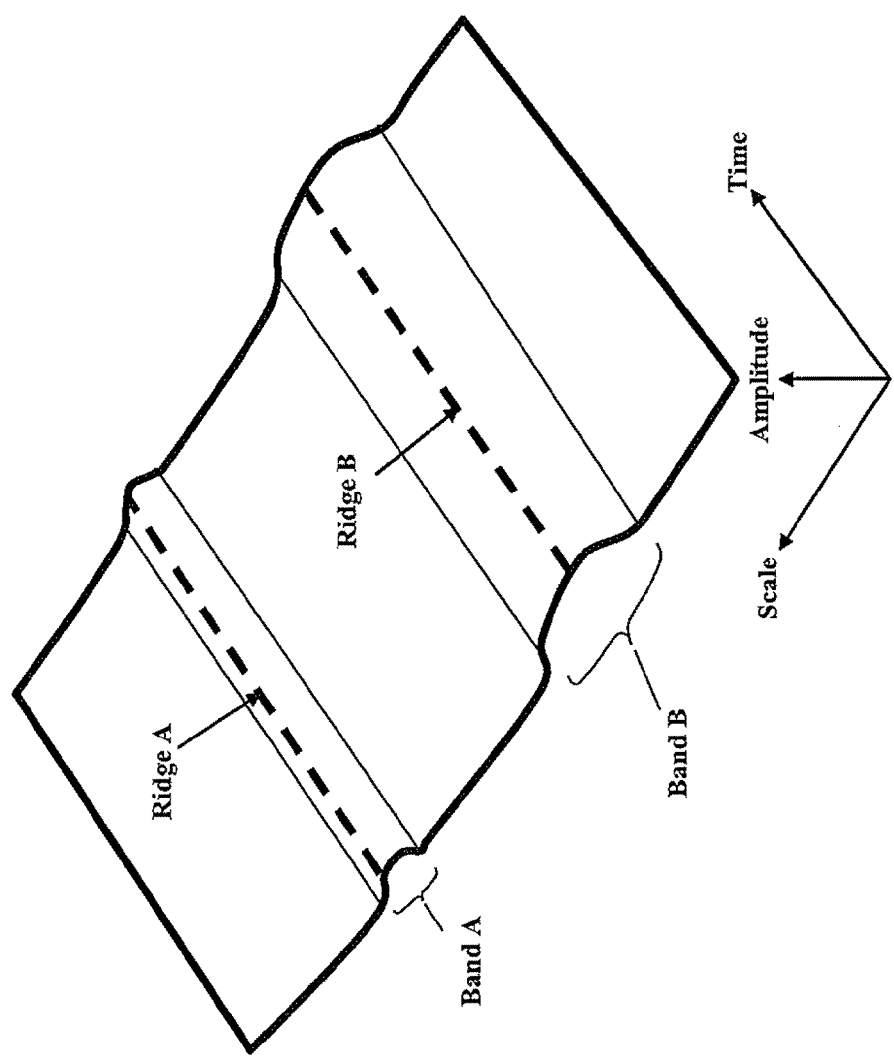
FIG. 3(c) shows an illustrative scalogram derived from a signal containing two pertinent components in accordance with an embodiment.
Figure 3D:
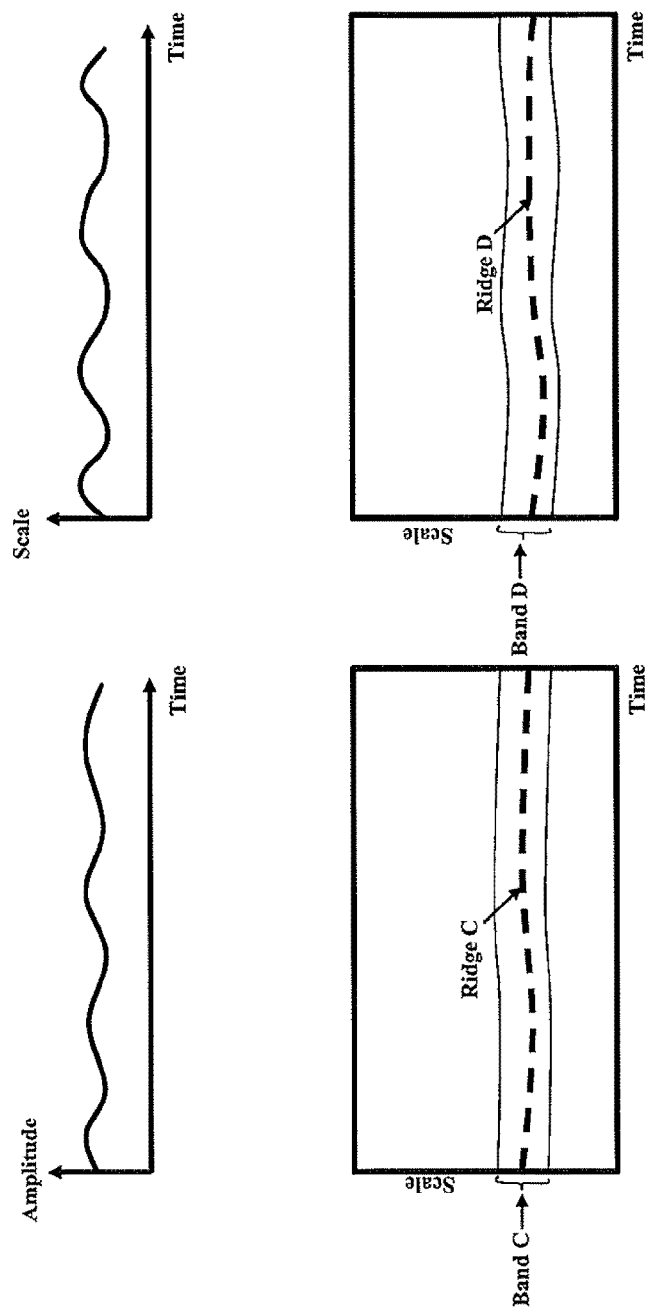
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \qquad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \qquad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \qquad (17)$$

Figure 3E:
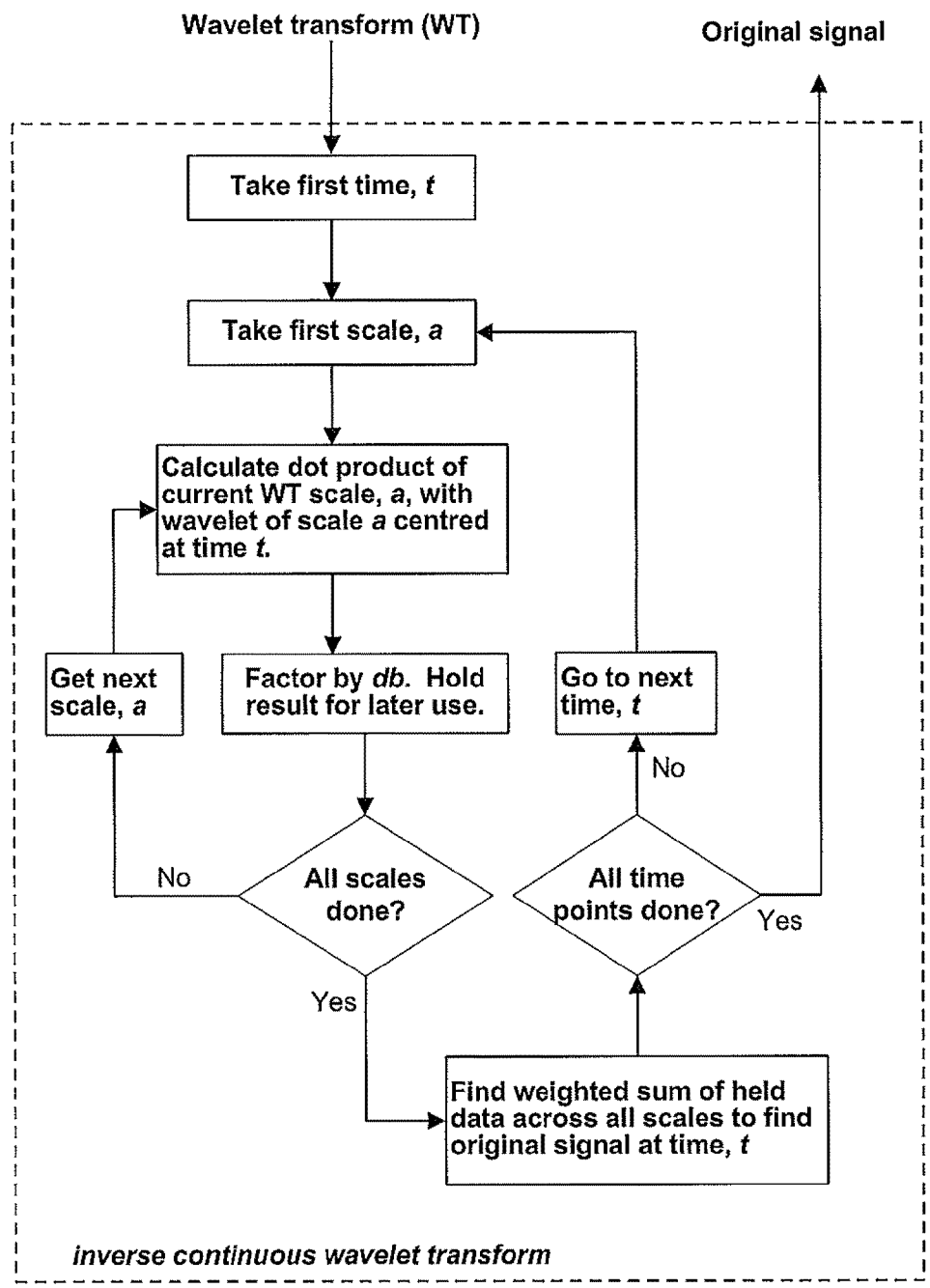
FIGS. 3(e) and 3(f) are flow charts of illustrative steps involved in performing an inverse continuous wavelet transform in accordance with embodiments.
Figure 3F:
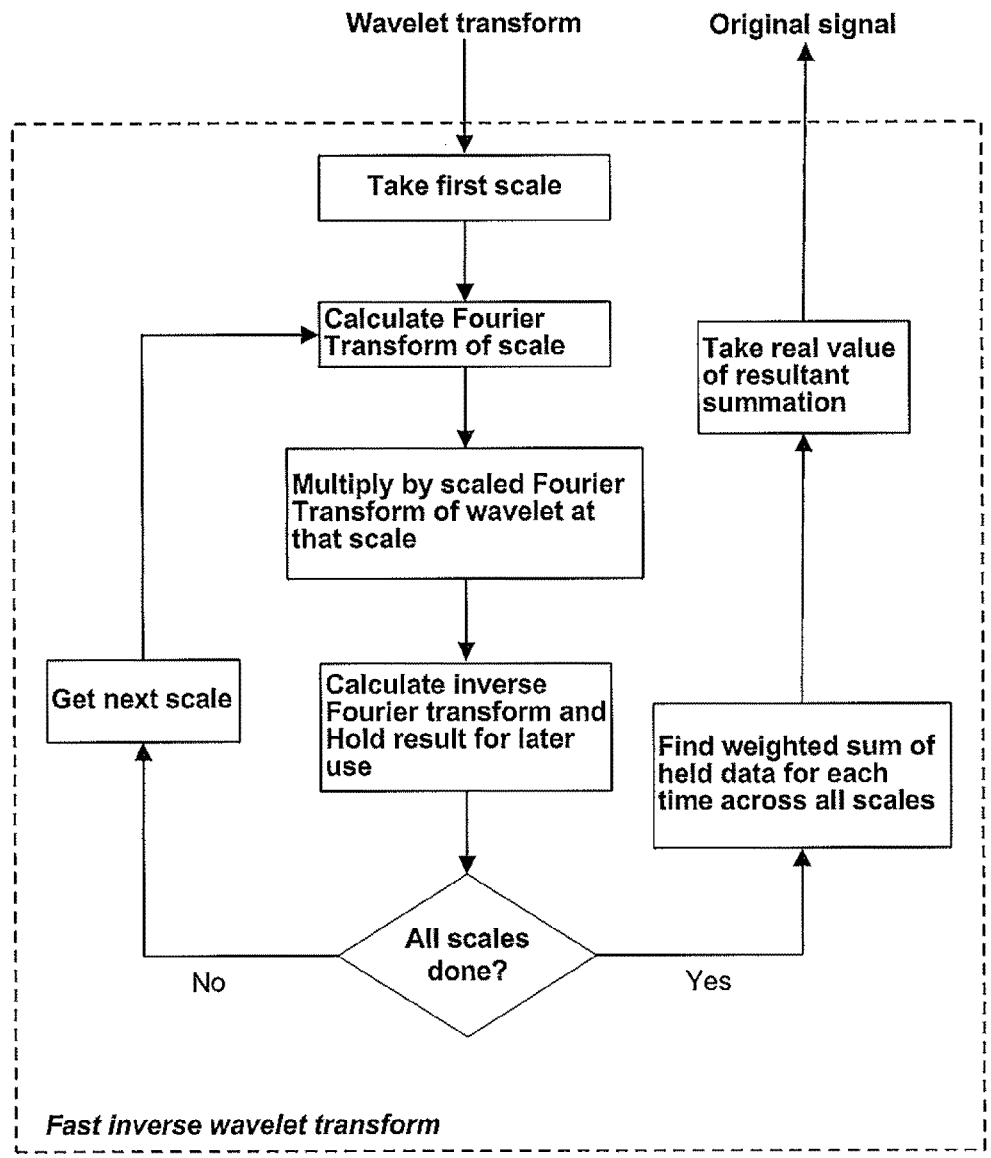

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The techniques described above, in particular, wavelet transformation, and scalogram analysis, may be used to determine respiration rate and respiration effort. In an embodiment, respiration effort may be found to relate to a measure of strength of at least one repetitive feature in a PPG signal. In another embodiment, effort may relate to physical effort of a process that may affect the signal (e.g. effort may relate to work of a process). Effort may also be determined by analyzing the signal representation. For example, changes in effort induce or change various features of the signal used to generate the scalogram. For example, the act of breathing may cause a breathing band to become present in a scalogram that was derived from a PPG signal. The breathing band may occur at or about a scale having a characteristic frequency that corresponds to the breathing frequency (respiration rate). Any features within this band or other bands on the scalogram (e.g., energy, amplitude, phase, or modulation) may result from changes in breathing and/or breathing effort and which may be correlated with the patient's breathing effort. Specific techniques for analyzing scalogram features for respiration effort are described in more detail in U.S. patent application Ser. No. 12/245,366, filed Oct. 3, 2008, entitled "SYSTEMS AND METHODS FOR DETERMINING EFFORT," the entire contents of which are incorporated by reference.

Figure 4:
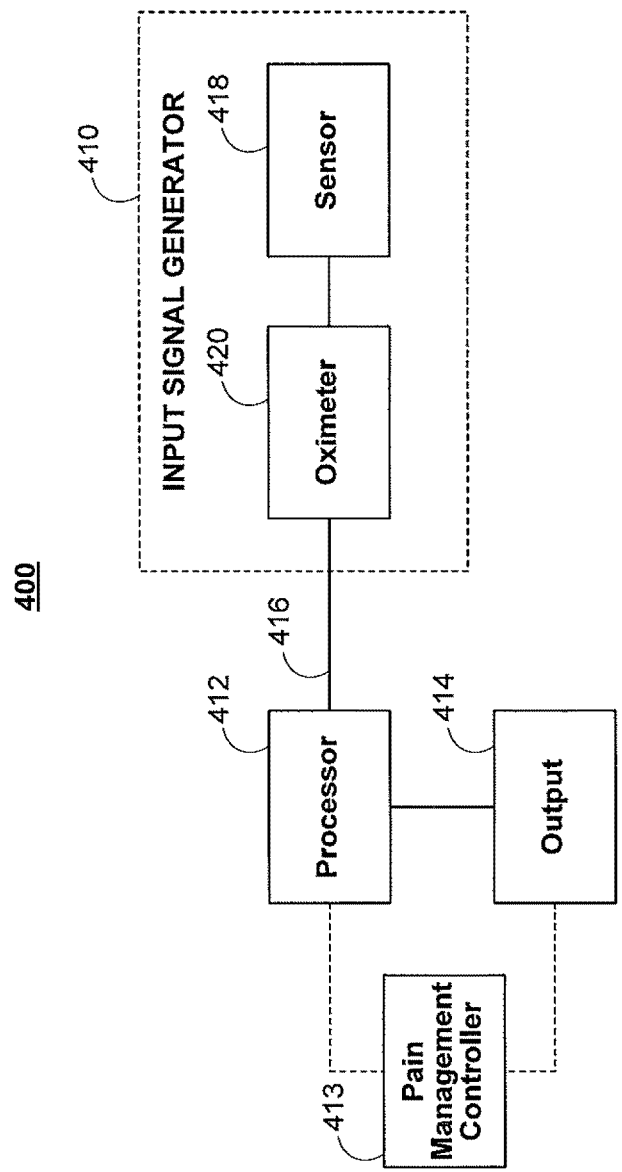
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

An optional pain management controller component 413 maybe coupled to processor 412 and output 414. The pain management controller 413 is configured to provide pain management specific signal processing as well as issuing a control signal to output 414. In an embodiment, such signal processing could also be provided by processor 412. Pain management specific signal processing may include processing of signals relating to pain management data, PPG signal information, such as input signal 416, as well as processing information relating to reference measurements or ranges for physiological parameters. Pain management controller 413 may also be coupled to a medication dispensation component (not shown), to which the pain management controller 413 may transmit a control signal indicating that pain medication may be required, increased, decreased, or other signal.

Pain management controller 413 and processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, for example, in order to determine respiration effort, processor 412 may first transform the signal into any suitable domain, for example, a Fourier, wavelet, spectral, scale, time, time-spectral, time-scale domains, or any transform space. Processor 412 may further transform the original and/or transformed signals into any of the suitable domains as necessary. Processor 412 may represent the original or transformed signals in any suitable way, for example, through a two-dimensional representation or three-dimensional representation, such as a spectrogram or scalogram.

After processor 412 represents the signals in a suitable fashion, processor 412 may then find and analyze selected features in the signal representation of signal 416 to determine effort. Selected features may include the value, weighted value, or change in values with regard to energy, amplitude, frequency modulation, amplitude modulation, scale modulation, differences between features (e.g., distances between ridge amplitude peaks within a time-scale band).

For example, selected features may include features in a time-scale band in wavelet space or a resealed wavelet space described above. As an illustrative example, the amplitude or energy of the band may be indicative of the breathing effort of a patient when the band is the patient's breathing band. Furthermore, changes in the amplitude or energy of the band may be indicative of a change in breathing effort of a patient. Other time-scale bands may also provide information indicative of breathing effort. For example, amplitude modulation, or scale modulation of a patient's pulse band may also be indicative of breathing effort. Effort may be correlated with any of the above selected features, other suitable features, or any combination thereof.

The selected features may be localized, repetitive, or continuous within one or more regions of the suitable domain space representation of signal 416. The selected features may not necessarily be localized in a band, but may potentially be present in any region within a signal representation. For example, the selected features may be localized, repetitive, or continuous in scale or time within a wavelet transform surface. A region of a particular size and shape may be used to analyze selected features in the domain space representation of signal 416. The region's size and shape may be selected based at least in part on the particular feature to be analyzed. As an illustrative example, in order to analyze a patient's breathing band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. For example, the expected locations may be based at least in part on empirical data of a plurality of patients. The region may also be selected based at least in part on patient classification. For example, an adult's breathing band location generally differs from the location of a neonatal patient's breathing band. Thus, the region selected for an adult may be different than the region selected for a neonate.

In some embodiments, the region may be selected based at least in part on features within a scalogram. For example, the scalogram for a patient may be analyzed to determine the location of the breathing band and its corresponding ridge. The breathing band ridge may be located using standard ridge detection techniques. Ridges may also be detected using the techniques described in Watson et al., U.S. application Ser. No. 12/245,326, filed Sep. 30, 2008, entitled "Systems and Method for Ridge Selection in Scalograms of Signals," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, the region may be determined based at least in part on the repetitive nature of the selected features. For example, a band may have a periodic feature. The period of the feature may be used to determine bounds of the region in time and/or scale.

The size, shape, and location of the one or more regions may also be adaptively manipulated using signal analysis. The adaptation may be based at least in part on changing characteristics of the signal or features within the various domain spaces.

As a signal is being processed, for example by processor 412 the region may be moved over the signal in any suitable domain space over any suitable parameter in order to determine the value or change in value of the selected features. The processing may be performed in real-time or via a previously recorded signal. For example, a region may move over the breathing band in the time-scale domain over time. When the selected features have been analyzed, they may be correlated with effort over time, and hence show the value or change in value of effort over time.

In some embodiments, the determined effort may be provided as a quantitative or qualitative value indicative of effort. The quantitative or qualitative value may be determined using the value or change in values in one or more suitable metrics of relevant information, such as the selected features mentioned above. The quantitative or qualitative values may be based on an absolute difference from a reference or a calibrated value of the features. For example, breathing effort of a patient may be calibrated upon initial setup. Alternatively, the values may be indicative of a relative change in the features such as the change in distance between peaks in amplitude, changes in magnitude, changes in energy level, or changes in the modulation of features.

The quantitative or qualitative value of effort may be provided to be displayed on a display, for example on display 28. Effort may be displayed graphically on a display by depicting values or changes in values of the determined effort or of the selected features described above. The graphical representation may be displayed in one, two, or more dimensions and may be fixed or change with time. The graphical representation may be further enhanced by changes in color, pattern, or any other visual representation.

The depiction of effort through a graphical, quantitative, qualitative representation, or combination of representations may be presented on output 414 and may be controlled by processor 412.

System 400 may be incorporated into system 10 (FIGS. 1 and 2) in which, for example, input signal generator 410 may be implemented as parts of sensor 12 and monitor 14 and processor 412 may be implemented as part of monitor 14. Arrangements of systems 400, 10 (FIGS. 1 and 2) may be used to provide a comprehensive pain management system as described herein.

Figure 5:
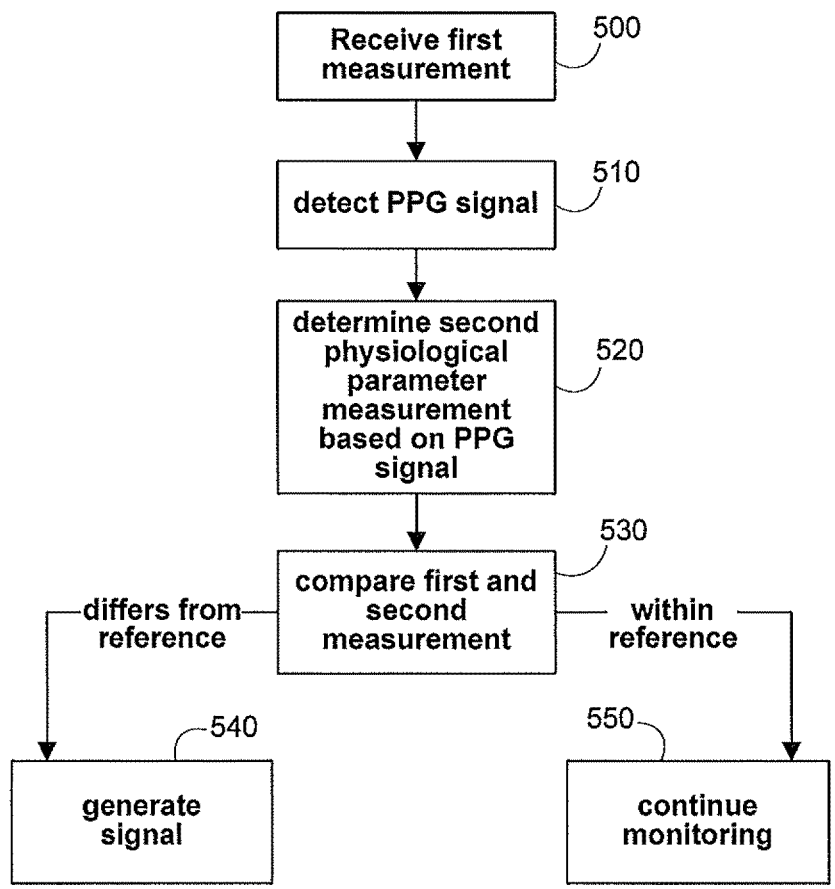
FIGS. 5-7 are flowcharts of methods for monitoring pain management in accordance with some embodiments.

In an embodiment, pain management monitoring may be provided using the steps of the flowchart depicted in FIG. 5. As shown, a reference measurement may be received at step 500. In some embodiments, a first or reference measurement may be received from calibration device 80 (FIGS. 1 and 2) based on reference information or other baseline data. In other embodiments, a reference measurement may be manually input, for example via calibration device 80 (FIGS. 1 and 2) or a user input component 56 (FIG. 2), encoder 42 (FIG. 1) or other suitable component. In other embodiments, a reference measurement may be calculated using processor 412 (FIG. 4) based on a signal 416 (FIG. 4) obtained using sensor 12 and monitor 14 (FIGS. 1 and 2). Generally speaking, the reference measurement may be a single value or range of values for one or more physiological parameters, such as blood pressure, respiration rate, respiration effort, pulse rate, or other parameter, that is suitable for providing a reference or benchmark for monitoring a patient's pain management. The reference measurement may be patient-specific, or a reference measurement that is appropriate for a similar cohort.

At step 510 a PPG signal may be detected. In an embodiment, the PPG signal may be detected by sensor 12 (FIGS. 1 and 2) that may be placed on a patient being monitored. In an embodiment, sensor 12 (FIGS. 1 and 2) is preferably a component that provides continuous readings, and which may be used to provide, for example, continuous non-invasive blood pressure measurements, or other measurements on a continuous basis.

The detected PPG signal may be used to determine a physiological parameter of the patient. For example, at step 520, blood pressure, or other physiological parameter may be determined based on the PPG signal 416 (FIG. 4) using, for example, processor 412 (FIG. 4). It will be understood that other types of physiological parameters, such as respiration effort, pulse rate, respiration rate, or other parameter could be determined by processor 412 (FIG. 4) at step 520 and equally or additionally applied to the methods for monitoring pain management discussed herein.

In an illustrative example, a blood pressure measurement determined at step 520 may be derived based on a signal 416 (FIG. 4) received from a sensor 12 (FIGS. 1 and 2), which may be a CNIBP device, using any of the techniques described herein, or a technique known in the art. For example, blood pressure may be calculated based on an elapsed time, T, between the arrival of corresponding points of a pulse signal at two locations using the two sensors 12 (FIGS. 1 and 2). In the case that a single sensor 12 (FIGS. 1 and 2) is used, the single probe or sensor may detect a PPG signal which may then be analyzed and used to compute a time difference between two or more characteristic points in the PPG signal. Analysis of the PPG signal and calculations of physiological parameters based on the PPG signal may be provided by processor 48 (FIG. 2) or 412 (FIG. 4) or other processing component.

At step 530 a comparison of the reference measurement and the determined physiological parameter measurement may be performed by processor 48 (FIG. 2) or 412 (FIG. 4). Generally speaking, for the comparison at step 530 the reference measurement is the reference measurement received at step 500 and the physiological parameter measurement is the measurement determined at step 520. In some embodiments, the comparison at step 530 may be performed using two physiological parameter measurements taken at different times while monitoring a patient. The comparison at step 530 may include a straight comparison of reference and blood pressure values, or any combination of comparative techniques that may include comparing an acceptable range of suitable baseline values. In addition, a comparison at step 530 may include comparisons of reference and determined values for more than one physiological parameter. For example, a comparison at step 530 may include comparing blood pressure measurements and respiration effort. Certain reference values may be used for such a comparison of a plurality of physiological parameters and may include varying acceptable ranges.

If the determined physiological measurement (or measurements) is found to differ from the reference measurement, for example, exceed or be less than an acceptable range of values for the reference, a signal may be generated at step 540. The signal generated at step 540 may be generated by processor 48 (FIG. 2) or 412 (FIG. 4) for output to 414 (FIG. 4) and may include an alarm that may be audible via speaker 22 (FIG. 1), displayed on monitor 28 (FIG. 1), or otherwise manifested. Other types of signals generated at step 540 may include a signal that may indicate that pain medication or other pain management treatment may be needed. Such a signal may be transmitted to a pain management controller 413 (FIG. 4) that may be communicatively coupled to the processor 48 (FIG. 2) or 412 (FIG. 4) that may automatically control dispensation of pain medication to a patient, or provide an indication to a medical provider that pain medication is required.

In the event that the blood pressure management is determined to be equivalent to or below the reference measurement, or within an acceptable range of reference values, the system 10 (FIG. 1) or 400 (FIG. 4) may continue monitoring the patient, at step 550. Continuing monitoring of the patient may include determining subsequent physiological parameter measurements and comparing the subsequent measurements to a reference measurement or other measurements to identify any changes in physiological parameters that may indicate a pain management problem. For example, continuous blood pressure measurements may be obtained using a CNIBP technique. The CNIBP measurements may be compared against a reference baseline or against prior CNIBP values to identify changes in blood pressure that may indicate a pain management problem.

Figure 6:
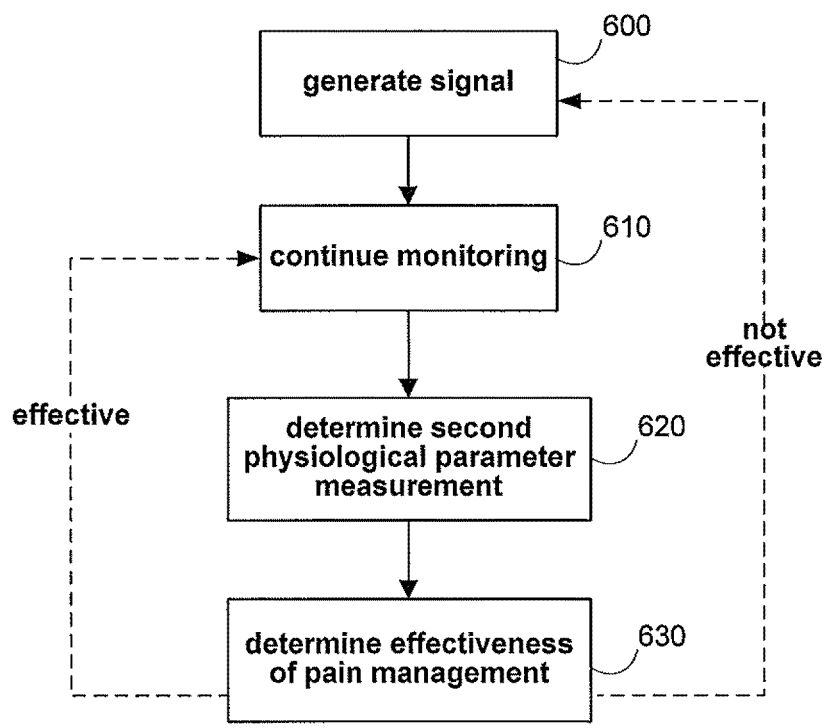

Such continuous monitoring may also be implemented following the signal generation at step 540 as shown in FIG. 6. Turning to FIG. 6, a signal may be generated at step 600 in a manner similar to that described in connection with step 540, such as generating an audible or visible alarm, or other signal. Such signal may be generated by a pain management controller 413 (FIG. 4) or processor 412 (FIG. 4) and sent to output 414 (FIG. 4). At step 610, monitoring of the patient may continue after the signal generation, for example, by continuing to receive signals 416 (FIG. 4) from a sensor 418 (FIG. 4) or 12 (FIGS. 1 and 2). The continued monitoring of the patient generally provides additional PPG signal information that may be used to determine a second or other following physiological parameter measurement at step 620. Comparisons of the second or following physiological parameter may be made against earlier measurements and a reference measurement. As mentioned above, ranges of values for comparative reference may be used. In addition, one or more physiological parameters and one or more periodic values of each may be compared in a continuing monitoring process to identify a change in the patient's physiological condition. The comparisons may be used to determine an effectiveness of a patient's pain management routine at step 630. For example, for a patient whose physiological parameter measurements fall within a suitable range or that do not differ from a reference measurement (for example, by more than a selected amount), pain management be determined to be effective, as further described herein. In such a case, monitoring may continue at step 610. For a patient whose physiological parameter measurements differ from suitable ranges or references may be determined to have a pain management problem, or that the pain management is not effective. In this case, additional measurements may be determined for confirmation purposes. Alternatively, or in addition, a signal may be generated to output 414 (FIG. 4), again at step 600 such as an alarm or indication that pain management may be required. Effectiveness of ongoing pain management treatment may also be provided using continuing monitoring methods as described herein. For example, if a patient has been identified as having a pain management problem, monitoring may be undertaken after additional pain management treatments or medication is provided to ensure that the additional measures are adequate or effective.

Figure 7:
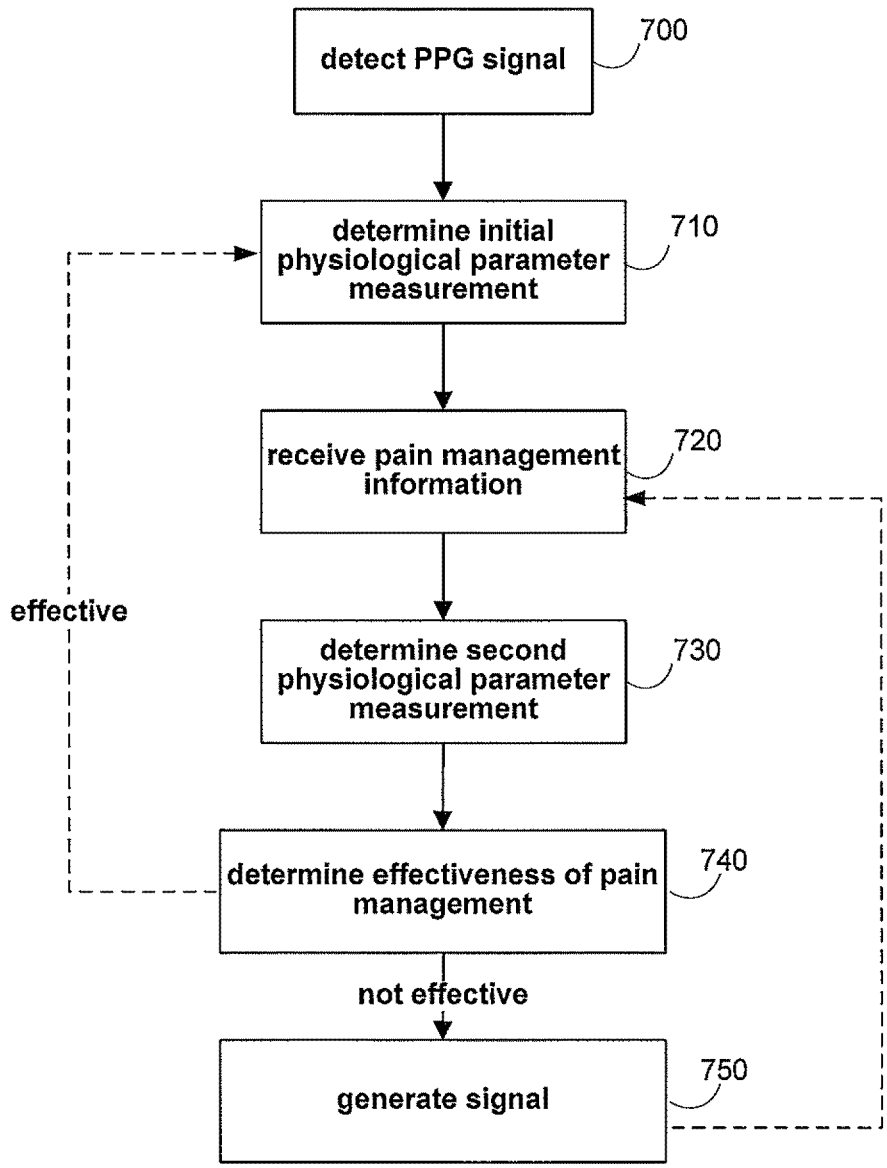

Such an approach is further described in connection with FIG. 7 which depicts a flowchart for monitoring pain management effectiveness. A PPG signal may be detected at step 700. The PPG signal may be detected by a sensor 418 (FIG. 4) or 12 (FIGS. 1 and 2) and used to determine an initial physiological parameter measurement at step 710. As discussed previously, the physiological parameter may be determined using any technique described herein, or known in the art. For example, respiration rate and respiration effort may be determined by analyzing features of a scalogram using processor 48 (FIG. 2) or 412 (FIG. 4) derived from the PPG signal 416 (FIG. 4). Respiration rate and effort may be of particular importance in ascertaining effectiveness of a pain management routine because increased and decreased respiration rate and effort may be indicative of a problem. Respiration rate and respiration effort measurements are useful in combination with blood pressure information because a heavily sedated individual's blood pressure may be normal to low which would not indicate a pain management problem. However, a patient with normal to low blood pressure and high respiration effort may have received excessive pain medication. Such a scenario could cause a signal to be transmitted to output 414 (FIG. 4) indicating that a reduction in pain medication or sedation would be appropriate.

A pain management controller 413 (FIG. 4) may receive information about pain management at step 720. Pain management information may include information such as an indication that a pain treatment has been administered, an indication that pain treatment may be needed, or other information. For example, pain management information may be information indicating that a patient has recently received a sedative, or that the patient has recently received a reduced pain medication dose. To ensure that the sedative is an appropriate treatment, a second measurement of the physiological parameter(s) may be determined at step 730. The second measurement may be determined using the technique used at step 710 or other technique. The second measurement may be compared against the initial measurement determined at step 720 or a baseline reference to determine whether the pain management treatment is effective at step 740. In particular, if the patient's physiological parameter measurements fall within an acceptable range or at or below a suitable benchmark, a pain management treatment may be determined to be effective. In this case, continued monitoring may be performed by returning to step 710. In the event that the pain management treatment is found not to be effective, a signal may be generated at step 750 and sent to output 414 (FIG. 4). The signal may be, for example, an alarm or an indication that pain management is not effective. Following the signal generation at step 750, monitoring may continue at step 720.

Figure 8:
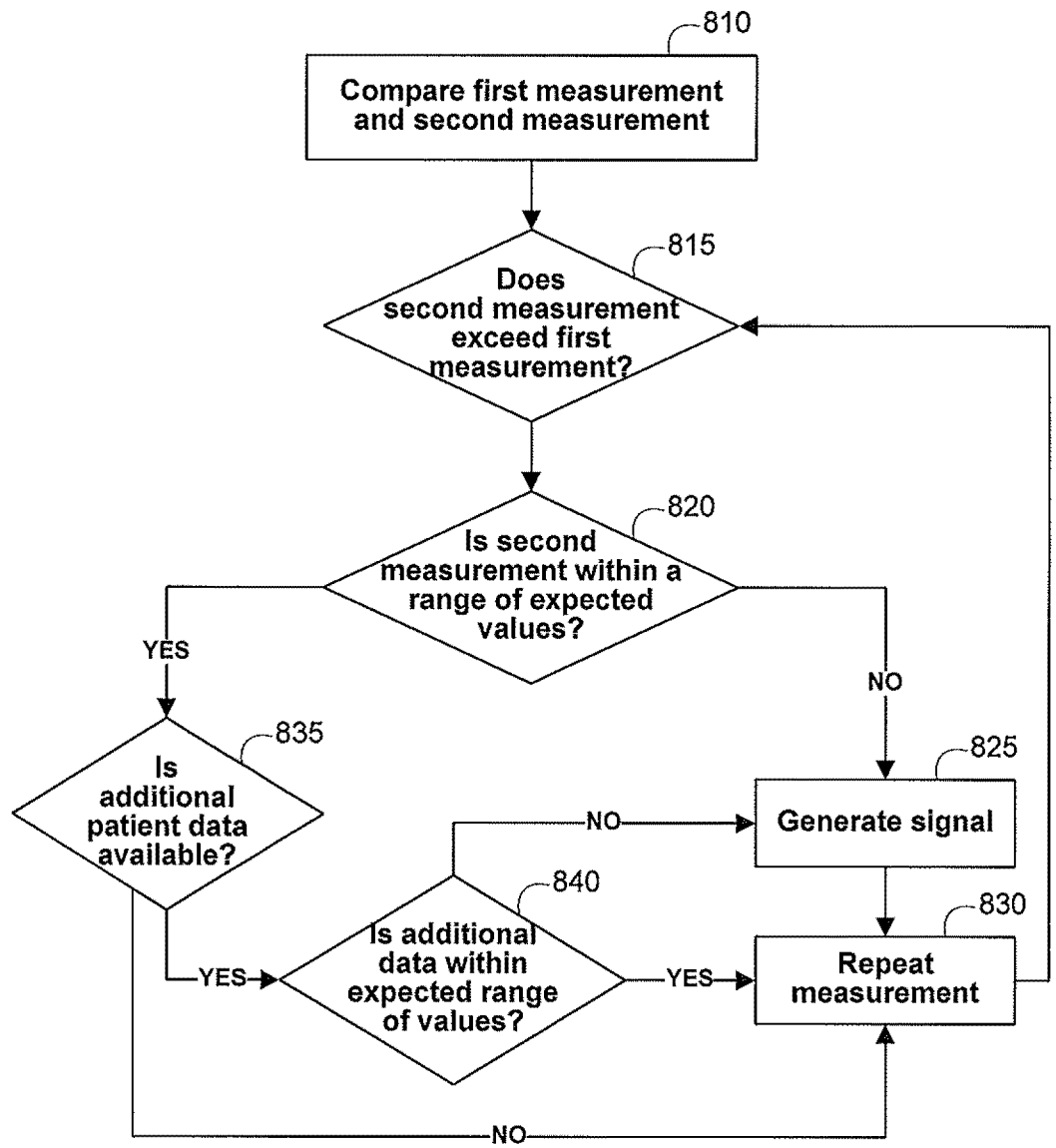
FIG. 8 is a flowchart of a method for determining effectiveness of pain management in accordance with some embodiments.

In an embodiment, pain management effectiveness may be determined following the steps of the flowchart depicted in FIG. 8. For example, at step 810, a first and second measurement may be compared. Typically, the first and second measurements may be obtained via calculations of a PPG signal 416 (FIG. 4) detected by sensor 418 (FIG. 4) or 12 (FIGS. 1 and 2), input as a reference value, or other measurement. As discussed previously, the measurements herein may be for any physiological parameter. For a pain management effectiveness determination, the first and second measurements are typically the same type of physiological parameter. The comparison at step 810 may be performed by processor 412 (FIG. 4) or other computing or processing component, and may include one or more inquiries. In an embodiment, the processor 412 (FIG. 4) determines whether the second measurement differs from the first measurement at step 815. For certain types of physiological parameters, such as respiration rate, problems may arise if the second measurement is less than the first measurement. In such a case, at step 815, the comparison inquiry may be whether the second measurement is less than the first. Either approach may be used.

In addition to, or instead of, step 815 the processor 412 (FIG. 4) may determine whether the second measurement is within a range of expected values at step 820. The expected values used in step 820 may be provided, for example, via user inputs 56 (FIG. 1), calibration device 80 (FIG. 1), pain management controller 413 (FIG. 4). The expected values may be a range of suitable values for a measurement, or a threshold for an expected change in a first and second value. If the second measurement is not within the range of expected values, a signal is generated at step 825. The signal generated at step 825 may be generated by processor 412 (FIG. 4) or pain management controller 413 (FIG. 4) and communicated to output 414 (FIG. 4), a pain medication dispenser component, or other component. The signal generated at step 825 typically indicates that a problem with pain management may exist, and the signal may include, for example, a signal indicating a visible or audible alarm. In other embodiments, the signal generated at step 825 may be an indication that a different or additional medication dose may be required. In some embodiments, the signal generated at step 825 may be a control signal for a pain medication dispenser to administer a dose of medication. Generally following a signal generation at step 825, monitoring of a patient continues by repeating a measurement sample at step 830. In a preferred embodiment, the measurements are repeated on a continual basis, and comparisons may be repeated, for example at steps 810 and 815.

If at step 820 the second measurement is determined by the processor 412 (FIG. 4) or pain management controller 413 (FIG. 4) to be within an expected range of values, additional information about a patient may be consulted if it is available at step 835. Additional patient data may include pain management treatment dosage history, prior measurements, additional data about a patient's pain management requirements, or other patient data. If no additional patient data is available, monitoring continues with repeated measurements, at step 830. If the additional patient data is available and within a certain expected range of values at step 840, monitoring will also continue with repeated measurements at step 830. If however, the additional patient data is available and does not fall within an expected range of values, a signal may be generated at step 825 indicating that a problem may exist. In an embodiment, determining effectiveness of pain management is a multi-faceted calculation that can be adapted to one or more different types of physiological parameters, as well as to a plurality of treatments.

Figure 9:
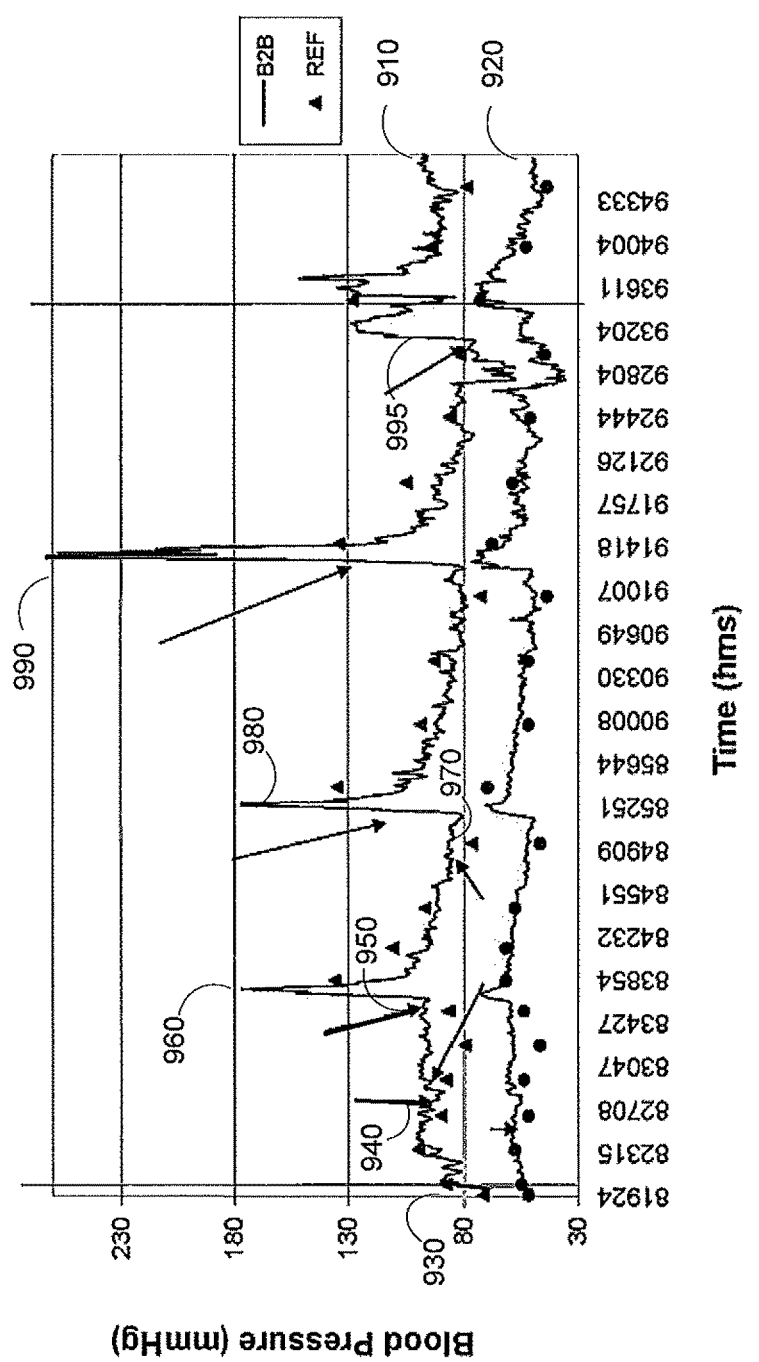
FIG. 9 is a diagram of illustrative blood pressure measurements in accordance with some embodiments.

An illustrative example of the effect of pain and pain treatment on blood pressure is depicted in FIG. 9 which shows a patient's systolic blood pressure at the upper line 910 and diastolic blood pressure at lower line 920 over time during a surgical operation. The chart in FIG. 9 was produced during a hip replacement surgery using a CNIBP monitoring device. Initial measurements for the patient's blood pressure are determined beginning at 8:19. The surgery start time was at point 930. As can be seen, the patient's blood pressure did not immediately change upon commencement of the surgery. At point 940, epinephrine, a routine treatment for anesthesia, was administered to the patient. At point 950, the patient's hip joint was removed from its socket, which caused the following increase in blood pressure at point 960. The pain associated with the hip joint removal appears to have been fleeting as the patient's blood pressure reduced to levels similar to those before surgery began. However, at point 970 cautery was undertaken causing another increase in blood pressure. Following the blood pressure increase at point 970, a sedative and other medication was administered to the patient at point 980 resulting a decrease in the patient's blood pressure. Pain relief and/or the drugs associated with pain relief may be accompanied by vasodilation or a reduction in blood pressure or both, which effects may be picked up by a CNIBP monitor. As the surgery continued, additional increases in blood pressure were determined at points 990 and 995 that were used to provide a signal to administer additional pain treatments to the patient. As can be seen from FIG. 9 continuous monitoring of a patient's blood pressure may be used to gauge effectiveness of pain management. In addition, the continuous monitoring of a patient's blood pressure may be useful feedback for self-administered pain management treatments. For example, for a patient that is self-administering pain medication, the blood pressure readings may be a useful reference to determine whether the pain medication is sufficient, excessive, or insufficient. Similarly, other physiological parameters may also be used as a reference for self-administering pain treatments.

Figure 10:
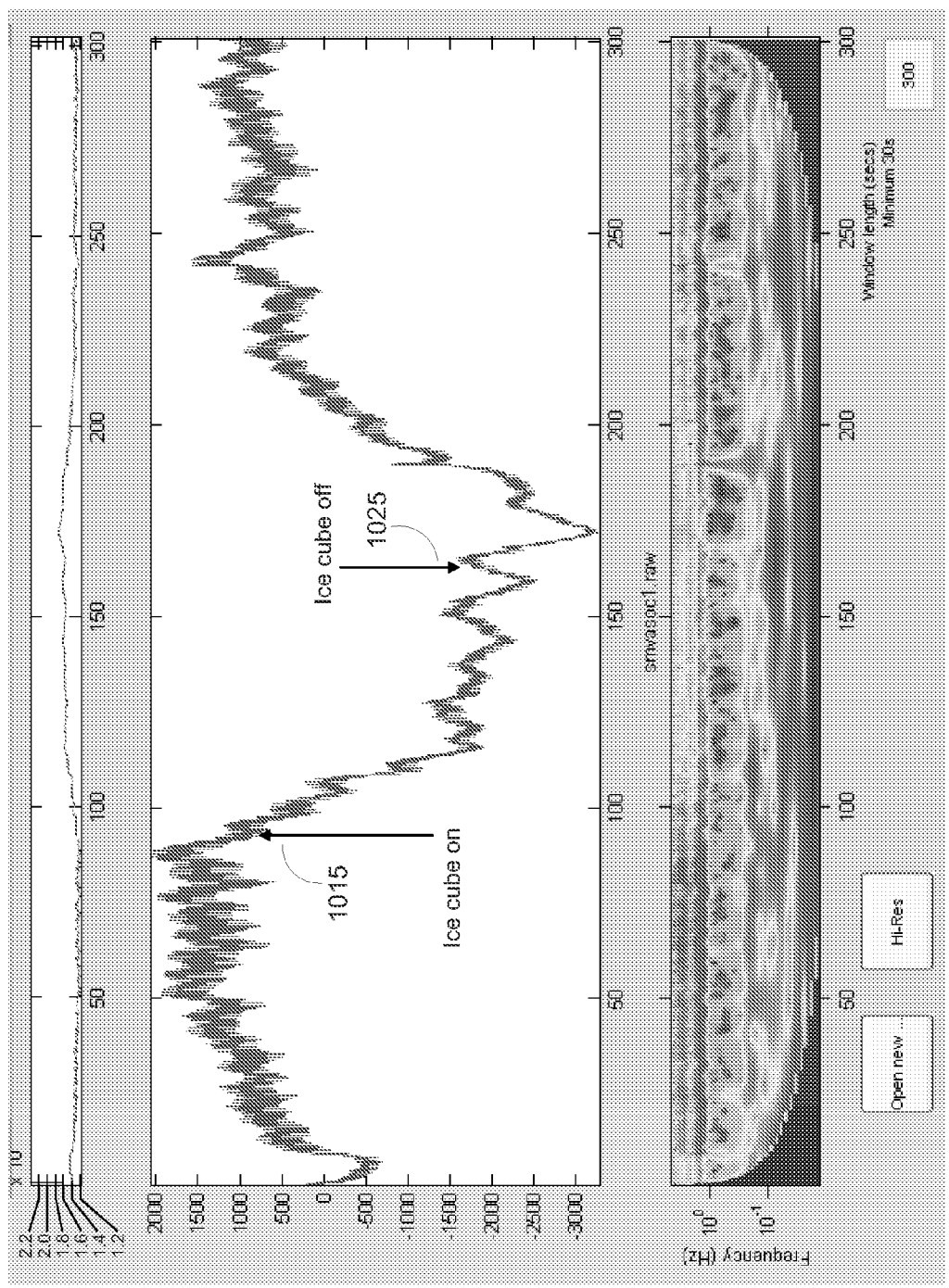
FIG. 10 is an illustrative PPG signal and scalogram in accordance with some embodiments.

In another example, a shape or features of a scalogram derived from a PPG signal may be used to identify changes in physiological parameters that may indicate a pain management problem. FIG. 10 depicts a scalogram derived from a PPG signal. The signal used in the scalogram shown in FIG. 10 is oriented so that the systolic peak is a maximum on the signal pulse, i.e., it is inverted from the incoming signal. This signal orientation is representative of absorption of the light. The original orientation of the signal could also be used, in which case, the baseline shifts would be in a direction opposite to the shifts shown in FIG. 10. The scalogram in FIG. 10 may be derived by processor 48 (FIG. 2) or 412 (FIG. 4) based on a PPG signal detected by sensor 12 (FIGS. 1 and 2). Certain features of the PPG signal and resulting scalogram may be used to identify changes in a physiological condition.

Such features may include a shape or morphology, scale or amplitude of the signal. For example, as shown in FIG. 9 a high scale of the PPG signal appears at time 0 to point 1015 at which time an ice cube was placed on a patient. Following placement of the ice cube, the signal baseline lowers and the amplitude of the individual pulse signals reduces. The signal baseline shift and amplitude reduction may be indicative of vasoconstriction, which is an indication that pain relief may be needed. Shortly, after the ice cube is removed at point 1025 the signal amplitude increase and baseline shift. The shift in the baseline characteristics of the PPG may indicate that vasodilation is occurring. Monitoring a PPG signal baseline shift may also be used for monitoring a patient's condition following administration of a pain relief treatment.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for monitoring pain management, comprising:
   receiving, at a processor, a first effort measurement;
   detecting, using a sensor, a PPG signal;
   analyzing, using the processor, one or more features within the PPG signal;
   determining, using the processor, a second effort measurement based at least in part on the one or more analyzed features;
   comparing, using the processor, the second effort measurement and at least the first effort measurement; and
   if the second effort measurement differs from the first effort measurement by a selected value, generating a signal.

2. The method of claim 1 further comprising generating, using the processor, a scalogram based at least in part on the PPG signal.

3. The method of claim 1 wherein the receiving a first effort measurement comprises receiving an input indicating an effort range, or receiving reference effort information based on the PPG signal.

4. The method of claim 1 wherein the signal indicates at least one of the group of: an alarm, a request to provide pain management, and a request to provide sedation.

5. The method of claim 1, further comprising, if the second effort measurement differs from the first effort measurement by a selected value, automatically providing pain management or sedation by sending a signal to a pain management controller indicating a request for pain management or sedation.

6. The method of claim 5, further comprising:
   determining, using the processor, a third effort measurement based at least in part on the PPG signal; and
   determining, using the processor, an effectiveness of the pain management or sedation based at least in part on the second effort measurement and the third effort measurement.

7. The method of claim 6, wherein the determining, using the processor, the effectiveness of the pain management or sedation is further based at least in part on data indicating a blood pressure measurement or a respiration rate.

8. A method for monitoring pain management, comprising:
   analyzing, using a processor, one or more features of a PPG signal;
   determining, using the processor, a first effort measurement based at least in part on the one or more analyzed features of the PPG signal;

receiving information at the processor indicating that pain management or sedation has been administered to a patient;
determining, using the processor, a second effort measurement based at least in part on the PPG signal at a time after the pain management or sedation has been administered to a patient; and
determining, using the processor, an effectiveness of the pain management or sedation based at least in part on a comparison of the first effort measurement and the second effort measurement.

9. The method of claim 8 further comprising, if the pain management or sedation is determined to not be effective: generating a signal comprising at least one of the group of: indicating an alarm, indicating a request to provide pain management, and indicating a request to provide sedation.

10. The method of claim 8, wherein the determining, using the processor, the effectiveness of the pain management or sedation is further based at least in part on data indicating a blood pressure measurement or a respiration rate.

11. A system for monitoring pain management, comprising:
a sensor having at least one emitter and at least one detector configured to detect a PPG signal, the sensor coupled to a processor and control circuitry configured to:
receive a first effort measurement;
analyze one or more features within the PPG signal;
determine a second effort measurement based at least in part on the one or more analyzed features of the PPG signal;
compare the second effort measurement and at least the first effort measurement; and
if the second effort measurement differs from the first effort measurement by a selected value, generate a signal.

12. The system of claim 11 wherein the control circuitry is further configured to generate, a scalogram based at least in part on the PPG signal.

13. The system of claim 11 wherein the received first effort measurement comprises receiving an input indicating a effort range, or receiving reference effort information based at least in part on the PPG signal.

14. The system of claim 11 wherein the signal indicates at least one of the group of: an alarm, a request to provide pain management, and a request to provide sedation.

15. The system of claim 11, further comprising, if the second effort measurement differs from the first effort measurement by a selected value, the control circuitry is further configured to automatically provide pain management or sedation by sending a signal to a pain management controller indicating a request for pain management or sedation.

16. The system of claim 15, wherein the control circuitry is further configured to determine a third effort measurement based at least in part on the PPG signal; and determine an effectiveness of the pain management or sedation based at least in part on the second effort measurement and the third effort measurement.

17. The system of claim 16, wherein the determining, using the processor, the effectiveness of the pain management or sedation is further based at least in part on data indicating a blood pressure measurement or a respiration rate.

18. A system for monitoring pain management, comprising:
a sensor having at least one emitter and at least one detector configured to detect a PPG signal, the sensor coupled to a processor and control circuitry configured to:
analyze one or more features of the PPG signal;
determine a first effort measurement based at least in part on the one or more analyzed features of the PPG signal;
receive information indicating that pain management or sedation has been administered to a patient;
determine a second effort measurement based at least in part on the PPG signal at a time after the pain management or sedation has been administered to a patient; and
determine an effectiveness of the pain management or sedation based at least in part on a comparison of the first effort measurement and the second effort measurement.

19. The system of claim 18 wherein the control circuitry is further configured, if the pain management or sedation is determined to not be effective, to generate a signal comprising at least one of the group of: indicating an alarm, indicating a request to provide pain management, and indicating a request to provide sedation.

20. The system of claim 18, wherein the control circuitry is further configured to determine the effectiveness of the pain management or sedation based at least in part on data indicating a blood pressure measurement or a respiration rate.

* * * * *